United States Patent
Allen et al.

(10) Patent No.: US 10,062,032 B2
(45) Date of Patent: *Aug. 28, 2018

(54) QUESTION RESOLUTION PROCESSING IN DEEP QUESTION ANSWERING SYSTEMS

(71) Applicant: International Business Machines Corporation, Armonk, NY (US)

(72) Inventors: Corville O. Allen, Morrisville, NC (US); Adam T. Clark, Mantorville, MN (US); Jeffrey K. Huebert, Rochester, MN (US); Aspen L. Payton, Byron, MN (US); John E. Petri, St. Charles, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 550 days.

This patent is subject to a terminal disclaimer.

(21) Appl. No.: 14/306,464

(22) Filed: Jun. 17, 2014

(65) Prior Publication Data

US 2015/0234825 A1    Aug. 20, 2015

Related U.S. Application Data

(63) Continuation of application No. 14/185,148, filed on Feb. 20, 2014.

(51) Int. Cl.
  *G06N 5/04* (2006.01)
  *G06F 17/30* (2006.01)
  *G16H 10/20* (2018.01)

(52) U.S. Cl.
  CPC ......... *G06N 5/04* (2013.01); *G06F 17/30654* (2013.01); *G16H 10/20* (2018.01)

(58) Field of Classification Search
  None
  See application file for complete search history.

(56) References Cited

U.S. PATENT DOCUMENTS

| | | |
|---|---|---|
| 6,289,330 B1 | 9/2001 | Jannarone |
| 2010/0274753 A1 | 10/2010 | Liberty et al. |
| 2012/0078888 A1 | 3/2012 | Brown et al. |
| 2012/0084112 A1 | 4/2012 | Bagchi et al. |

(Continued)

OTHER PUBLICATIONS

A. Kalyanpur, B. K. Boguraev, S. Patwardhan, J. W. Murdock, A. Lally, C. Welty, J. M. Prager, B. Coppola, A. Fokoue-Nkoutche, L. Zhang, Y. Pan, Z. M. Qiu, "Structured Data and Inference in DeepQA", IBM J. Res. & Dev. vol. 56 No. 3/4 Paper 10, May/Jul. 2012, pp. 10:1-10:14.*

(Continued)

*Primary Examiner* — Alan Chen
(74) *Attorney, Agent, or Firm* — Patterson + Sheridan, LLP

(57) ABSTRACT

System, method, and computer program product for performing an operation, the operation comprising receiving, by a deep question answering system, a question not specifying an element of input data, identifying a set of possible values for the element of input data, generating, by the deep question answering system, a respective set of candidate answers for the question: (i) without the element of input data, and (ii) with each possible value in the set of possible values for the element of input data, and returning at least one candidate answer from at least one set of candidate answers as responsive to the question.

8 Claims, 6 Drawing Sheets

(56) References Cited

U.S. PATENT DOCUMENTS

2015/0161241 A1* 6/2015 Haggar ............ G06F 17/30654
707/723
2015/0235131 A1 8/2015 Allen et al.

OTHER PUBLICATIONS

J. W. Murdock, A. Kalyanpur, C. Welty, J. Fan, D. A. Ferrucci, D. C. Gondek, L. Zhang, H. Kanayama, "Typeing Candidate Answers Using Type Coercion", IBM J. Res. & Dev. vol. 56 No. 3/4 Paper 7 May/Jul. 2012, pp. 7:1-7:13.*

D. C. Gondek, A. Lally, A. Kalyanpur, J. W. Murdock, P. A. Duboue, L. Zhang, Y. Pan, Z. M. Qiu, C. Welty, "A framework for merging and ranking of answers in DeepQA", IBM J. Res. & Dev. vol. 56 No. 3/4 Paper 14 May/Jul. 2012, pp. 14:1-14:12.*

C. Wang, A. Kalyanpur, J. Fan, B. K. Boguraev, D. C. Gondek, "Relation Extraction and Scoring in DeepQA", IBM J. Research and Development, vol. 56, No. 3/4, paper 9, May/Jul. 2012, pp. 9:1-9:9.*

John M. Prager, Jennifer Chu-Carroll, Eric W. Brown and Krzysztof Czuba, "Question Answering by Predictive Annotation", Advances in Oopen Domain Question Answering, vol. 32 of Text, Speech and Language Technology, 2006, pp. 307-347.*

Deepak Ravichandran and Eduard Hovy, "Learning Surface Text Patterns for a Question Answering System", Proceedings of the 40th Annual Meeting of the Association for Computational Linguistics (ACL), Philadelphia, Jul. 2002, pp. 41-47.*

David Ferrucci, Eric Brown, Jennifer Chu-Carroll, James Fan, David Gondek, Aditya A. Kalyanpur, Adam Lally, J. William Murdock, Eric Nyberg, John Prager, Nico Schlaefer, and Chris Welty, "Building Watson: An Overview of the DeepQA Project", AI Magazine, Association for the Advancement of Artificial Intelligence, 2010, pp. 59-79.*

A. Kalyanpur et al., "Structured Data and Inference in DeepQA", IBM J. Res. & Dev. vol. 56 No. 3/4 Paper 10, May/Jul. 2012, pp. 10:1-10:14.

J. W. Murdock et al., "Typing Candidate Answers Using Type Coercion", IBM J. Res. & Dev. vol. 56 No. 3/4 Paper 7 May/Jul. 2012, pp. 7:1-7:13.

D. C. Gondek et al., "A framework for merging and ranking of answers in DeepQA", IBM J. Res. & Dev. vol. 56 No. 3/4 Paper 14 May/Jul. 2012, pp. 14:1-14:12.

U.S. Appl. No. 14/185,148, entitled "Question Resolution Processing in Deep Question Answering Systems", filed Feb. 20, 2014.

* cited by examiner

QUESTION RESOLUTION PROCESSING IN DEEP QUESTION ANSWERING SYSTEMS

CROSS-REFERENCE TO RELATED APPLICATIONS

This application is a continuation of co-pending U.S. patent application Ser. No. 14/185,148, filed Feb. 20, 2014. The aforementioned related patent application is herein incorporated by reference in its entirety.

BACKGROUND

Embodiments disclosed herein relate to the field of computer software. More specifically, embodiments disclosed herein relate to computer software that provides question resolution processing in deep question answering systems.

When users submit questions to deep question answering systems, pertinent information is extracted from the question in order to generate a set of candidate answers. Generally, the "best" answer is the candidate answer that the deep QA system has the most confidence in, namely, the candidate answer having the highest confidence score. Key pieces of "critical" information can greatly increase the confidence score of an answer. Conversely, the deep QA system may generate candidate answers having low confidence scores when the question does not specify values for elements of critical information.

However, when pieces of pertinent information are not included in the question, the deep question answering system generates a set of candidate answers that may have a low confidence score. As such, the answers generated by the deep question answering system in such a scenario may not be very useful, as indicated by the low confidence score for these answers.

SUMMARY

Embodiments disclosed herein provide at least a system, method, and computer program product for performing an operation, the operation comprising receiving, by a deep question answering system, a question not specifying an element of input data, identifying a set of possible values for the element of input data, generating, by the deep question answering system, a respective set of candidate answers for the question: (i) without the element of input data, and (ii) with each possible value in the set of possible values for the element of input data, and returning at least one candidate answer from at least one set of candidate answers as responsive to the question.

BRIEF DESCRIPTION OF THE SEVERAL VIEWS OF THE DRAWINGS

So that the manner in which the above recited aspects are attained and can be understood in detail, a more particular description of embodiments of the disclosure, briefly summarized above, may be had by reference to the appended drawings.

It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
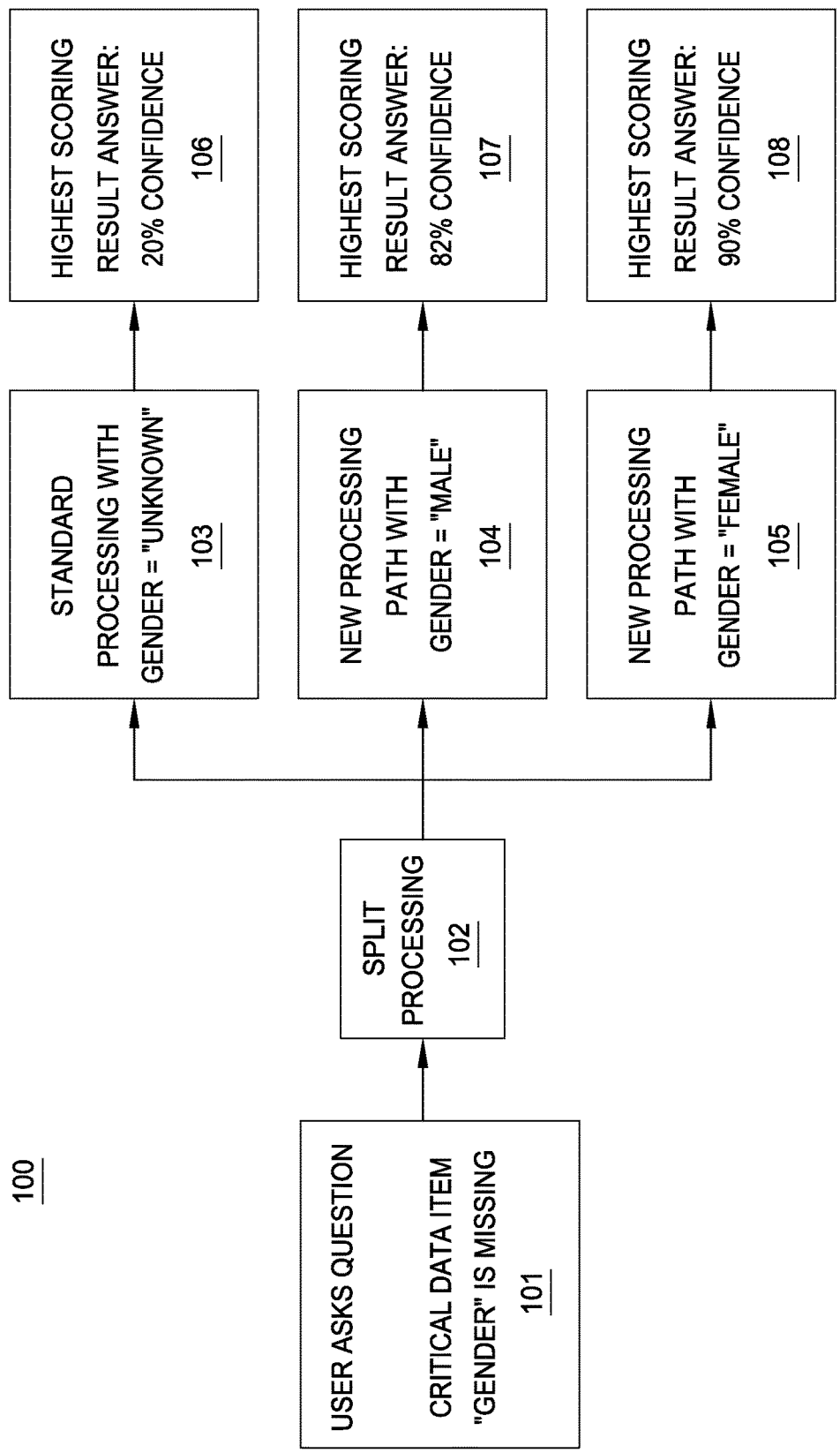
FIG. 1 illustrates techniques to implement question resolution processing in deep question answering systems, according to one embodiment.

Embodiments disclosed herein provide deep question answering (deep QA) systems configured to identify questions that do not specify values for pieces of "critical" data, and in response, implement a parallel processing approach to evaluate the questions with multiple alternative values in place of the unspecified critical data. For example, and without limitation, a user may ask the deep QA system "why do I have a pain in the side of my lower abdomen?" The deep QA system may determine that the user's failure to specify the side of their abdomen they are experiencing pain in means that a value for a "critical" piece of information is missing. In response, the deep QA system may then determine that the two possibilities for the unspecified critical data are "left" and "right" sides. The deep QA system may then process each variant of the question, namely where the side of the lower abdomen is "unknown," "left," and "right," in a respective parallel processing pipeline. The deep QA system may then return sets of candidate answers to the user based on each parallel processing pipeline. In one embodiment, the deep QA system may then ask the user which side of the abdomen hurts, which may then be used to select the highest scoring candidate answer from that parallel processing path. For example, if the user indicates that the pain is on his "right" side, then the deep QA system may return an answer indicating that the user may have appendicitis. The output produced by the deep QA system in this example is for illustrative purposes, and should not be considered limiting of the disclosure, as the deep QA system may generate any suitable output as being responsive to the question.

The parallel processing disclosed herein may allow the deep QA system to produce a set of candidate answers having higher confidence scores without requiring re-processing of the original question, as the parallel processing may produce results that encompass the correct answer for the true value of the unspecified (or "missing") critical data elements. In addition, based on training data analysis, certain unspecified critical data may trigger parallel processing if the unspecified critical data impacts confidence scores of the candidate answers beyond a specified threshold. Such an approach may allow the deep QA system to provide distinct answers based on additional information that would have caused the deep QA system to generate better answers or higher confidence in the generated answers. In addition, the deep QA system may identify alternative values for the unspecified critical data element values.

As used herein, the term "critical" data (also referred to as critical information and critical features) refers to data that is highly relevant in allowing a deep QA system to generate an accurate response to a question. Stated differently, values for the critical data, when present, may allow the deep QA system to generate candidate answers that have a higher confidence score than candidate answers the deep QA system may generate absent values for the critical data. Additionally, values for the critical data, when present, may enable the deep QA system to identify supporting evidence and candidate answers in a corpus of information that would not be discovered without the critical data. U.S. patent application Ser. No. 13/717,043, entitled "Question Classification and Feature Mapping in a Deep Question Answering System," herein incorporated by reference in its entirety, discusses how deep QA systems may identify critical data (or features).

FIG. 1 illustrates techniques to implement question resolution processing in deep question answering systems, according to one embodiment. Traditionally, when a user asks a question of a deep question answering system, the deep QA system processes the question as the user presented it. If the user failed to specify certain elements of information, the deep QA system processes the question without the information, regardless of how relevant or critical the information is in allowing the deep QA system to generate accurate responses.

As shown in FIG. 1, a user may ask a deep QA system a question at block 101. For example, and without limitation, the user may ask, "will I develop osteoporosis?" However, the user may have failed to specify (intentionally or unintentionally) a value for a critical data item, such as "gender," which may be highly relevant in allowing the deep QA system to generate an accurate response to the user's question. In order to allow the deep QA system to generate more accurate responses, embodiments disclosed herein may perform parallel split processing of the question, as depicted in block 102. The deep QA system may use any feasible method to identify that "gender" is critical data, such as feature classification during training of the QA system.

At block 103, the deep QA system implements standard processing of the question with a value for gender being unknown. As a result, the deep QA system produces a highest scoring candidate answer having a 20% confidence score. Advantageously, however, the deep QA system may, at blocks 104 and 105, trigger new processing pipelines of the question, each pipeline using alternate values for gender in the question. As shown, at block 104, the deep QA system triggers a new processing path for the question with the value of "male" for gender, while at block 105, the deep QA system triggers a new processing path for the question using the value of "female" for gender. The deep QA system may identify the alternate values by any feasible method, including, without limitation, referencing a store that includes the alternate values, and referencing a corpus of information to pull, from the data stored in the corpus, the different values for any piece of critical data. By substituting the different possible values for gender in the new processing pipelines, the deep QA system may be able to generate candidate answers having a higher confidence score than the results generated in block 106 with an unknown gender. As shown at block 107, the highest scoring candidate answer for generated using "male" as the gender has an 82% confidence score, while at block 108, the highest scoring candidate answer generated using "female" as the gender has a 90% confidence score.

Once the deep QA system completes processing each pipeline, it may return the results to the user in any feasible manner. For example, the deep QA system may generate a matrix of results that depicts the confidence score of each candidate answer generated by the processing pipelines using the different gender values as shown in Table I:

TABLE I

| Candidate Answer | Male | Female | Unknown |
|---|---|---|---|
| Answer 1 | 0.82 | 0.74 | 0.10 |
| Answer 2 | 0.70 | 0.90 | 0.08 |
| Answer 3 | 0.10 | 0.12 | 0.20 |

Without running the additional parallel processing pipelines, the deep QA system may return Answer 3 as the most best result, as it has the highest confidence score (20%) for each of the three candidate answers when processing the question with gender unknown. However, when supplying the alternate values of male and female, candidate Answers 1 and 2, respectively, are the highest scoring candidate answers (with 82% and 90% confidence scores, respectively). In addition to (or in lieu of) presenting the matrix, the deep QA system may then present the user an interface to lead the user through a series of questions to allow them to provide specific values for the unspecified critical data values (in this example, including at least one prompt to provide a value for gender).

Figure 2:
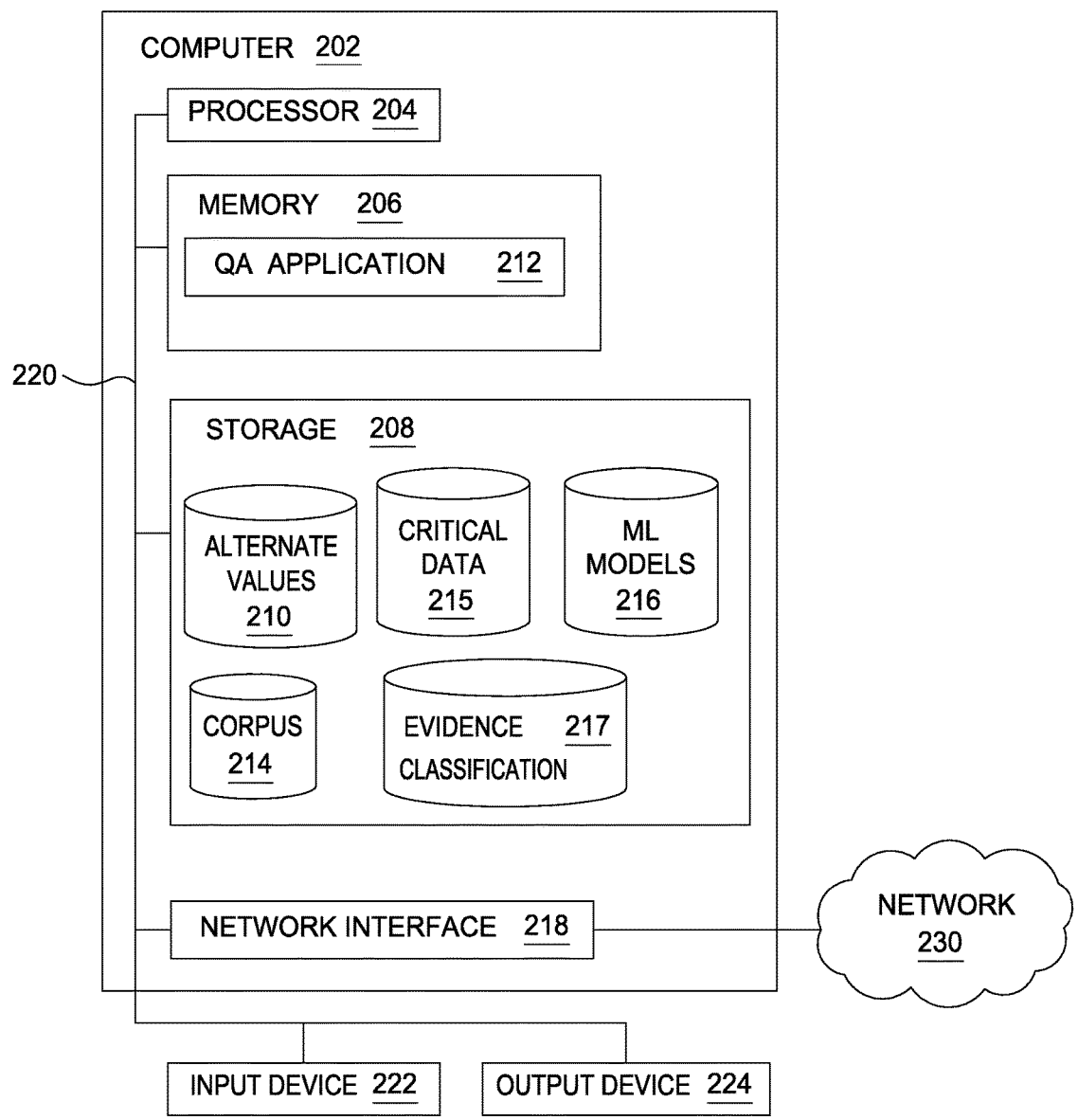
FIG. 2 is a block diagram illustrating a system implementing question resolution processing in deep question answering systems, according to one embodiment.

FIG. 2 is a block diagram illustrating a system 200 implementing question resolution processing in deep question answering systems, according to one embodiment. The networked system 200 includes a computer 202. The computer 202 may also be connected to other computers via a network 230. In general, the network 230 may be a telecommunications network and/or a wide area network (WAN). In a particular embodiment, the network 230 is the Internet.

The computer 202 generally includes a processor 204 connected via a bus 220 to a memory 206, a network interface device 218, a storage 208, an input device 222, and an output device 224. The computer 202 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 204 is included to be representative of a single CPU, multiple CPUs, a single CPU having multiple processing cores, and the like. Similarly, the memory 206 may be a random access memory. While the memory 206 is shown as a single identity, it should be understood that the memory 206 may comprise a plurality of modules, and that the memory 206 may exist at multiple levels, from high speed registers and caches to lower speed but larger DRAM chips. The network interface device 218 may be any type of network communications device allowing the computer 202 to communicate with other computers via the network 230.

The storage 208 may be a persistent storage device. Although the storage 208 is shown as a single unit, the storage 208 may be a combination of fixed and/or removable storage devices, such as fixed disc drives, solid state drives, floppy disc drives, tape drives, removable memory cards or optical storage. The memory 206 and the storage 208 may be part of one virtual address space spanning multiple primary and secondary storage devices.

The input device 222 may be any device for providing input to the computer 202. For example, a keyboard and/or a mouse may be used. The output device 224 may be any device for providing output to a user of the computer 202. For example, the output device 224 may be any conventional display screen or set of speakers. Although shown separately from the input device 222, the output device 224 and input device 222 may be combined. For example, a display screen with an integrated touch-screen may be used.

As shown, the memory 206 contains the QA application 212, which is an application generally configured to operate as a deep question answering (QA) system. One example of a deep question answering system is Watson, by the IBM Corporation of Armonk, N.Y. A user may submit a question (also referred to as a case) to the QA application 212, which will then provide an answer to the question based on an analysis of a corpus of information 214. The QA application 212 may analyze the question text to identify concepts in the question. Based on the analysis of the questions, the QA application 212 may identify a number of candidate answers. The QA application 212 may then find supporting evidence for the candidate answers. The QA application 212 may then score and rank the candidate answers, merge the results, and present the best answer as its response to the case.

Additionally, the QA application 212 may be configured to identify questions that do not specify values for critical data. The QA application 212 may identify the critical data by analyzing the question, identifying a context of the question, and using the context to determine one or more pieces of critical data based on relationships in the evidence classification 217. In addition, the QA application 212 may be "trained" to identify different pieces of critical data during training runs where the QA application 212 processes sample questions in order to identify which types of data impact the confidence score of generated candidate answers beyond a specified threshold. Thereafter, the QA application 212 may identify these elements of data that impact the confidence score of generated responses, and if values for these data elements are not specified in the question, the QA application 212 can trigger parallel processing using alternate values for the data elements. In some embodiments, multiple pieces of data may form a composite critical data element. For example, and without limitation, epidermal growth factor receptor (EGFR) mutation values combined with margin status may impact confidence over a threshold, and may therefore form a composite critical data element for predicting whether a patient may develop some types of cancer.

Once the QA application 212 determines that the question does not specify values for critical data, the QA application 212 may identify different possible values for the unspecified critical data. The different values may include, for example and without limitation, "male" and "female" for gender, specific age ranges (e.g., 0-6, 7-13, 14-18, etc), "adult," "senior," or "child," and the like. In one embodiment, the QA application 212 retrieves the possible values from the values 210. In another embodiment, the QA application 212 may identify the possible values from the corpus 214. The QA application 212 may identify the possible values in the corpus 214 by analyzing the data contained therein to identify specified values for the critical data. For example, a scholarly article may reference three age ranges for an age critical attribute in a certain context, such as 0-30, 31-60, and 61-90 years old. The QA application 212 may then identify these ranges, and store them in the values 210. The QA application 212 may continue to refine the different possible values stored in the values 210, for example, if new values are found to be relevant, or other values are determined not to be relevant. Furthermore, the QA application 212 may continue to monitor which data are indeed critical, and update the critical data store 215 and evidence classification 217 accordingly.

Once the QA application 212 identifies the possible data values, the QA application 212 may determine whether the total number of possible data values for the unspecified data element is less than a programmable threshold, in order to limit the number of parallel processing pipelines that may be triggered for each possible data value. For example, if the threshold is 10, and an item of critical data has 100 alternate values, the QA application 212 may not process each item in parallel in order to conserve system resources. Instead, in one embodiment, the QA application 212 may implement a clustering technique to merge variations into logical groups. For example, if the possible variations for age was any integer between 1 and 100, the QA application 212 may cluster the possible ages into decade-sized groups, or some other observed group. In another embodiment, the QA application 212 may not trigger parallel processing at all if the threshold value is exceeded in order to conserve system resources, and may only process the question without the values for the critical data elements.

If the QA application 212 determines that the possible values for the unspecified critical data elements are finite and small enough to trigger parallel processing, the QA application 212 may then trigger parallel processing pipelines for the question using each possible value for the critical data element. The QA application 212 may also process the question as provided by the user, without a value for one or more critical data elements. In processing each permutation of the question, the QA application 212 may analyze the question text, pull evidence from the corpus 214, and generate and score a number of candidate answers. Once the QA application 212 processes each question, the QA application 212 may present the results in any feasible manner. In one embodiment, the QA application 212 may present the complete set of results in a matrix. In another embodiment, the QA application 212 may output a subset of the results to the user. In still another embodiment, the QA application 212 may return a candidate answer as the best answer because the candidate answer has the highest confidence score for each possible value of the critical data element. For example, gender may be omitted from the question, and the QA application 212 may return the following results as shown in Table II:

TABLE II

| Candidate Answer | Male | Female | Unknown |
| --- | --- | --- | --- |
| Answer 1 | 0.85 | 0.92 | 0.30 |
| Answer 2 | 0.40 | 0.10 | 0.01 |
| Answer 3 | 0.10 | 0.20 | 0.50 |

As shown, if the user omitted gender, the QA application 212 may traditionally return Answer 3 as the best answer, as it has the highest confidence score of the candidate answers processed with an "unknown" value for gender. However, the QA application 212 may determine that for some data elements, such as gender, there are a limited number of possibilities, namely male and female. In such a case, regardless of which value is the correct value (male or female), Answer 1 is the correct answer. By automatically recognizing the finite number of possible values for some types of data, the QA application 212 may revise the answer list, and produce a better answer (in this example, Answer 1), without any intervention from the user. Furthermore, the scoring of Answer 1 may be driven by different corpus evidence when "male" is selected rather than "female," but either value is preferable to "unknown," as the evidence becomes unusable. For example, there may be one article about breast cancer in men, and another article about breast cancer in women. Both articles may indicate that their respective studies have shown value in a particular drug, but if no gender is specified, then the QA application 212 cannot determine that either of these articles applies to the question. Therefore, when the QA application 212 "guesses" as to the value of a piece of critical data, it may lead to the concrete selection of an answer different than an answer that the QA application 212 would have defaulted to using an unknown value for the critical data.

As shown, the storage 208 contains the values 210, corpus 214, critical data store 215, ML models 216, and evidence classification 217. The values 210 include a range of different values identified by the QA application 212 (or a user) as possible values for one or more critical data elements. The QA application 212 may identify the alternate values from the corpus 214 during processing of the question, or during a training phase of the QA application 212. The corpus 214 is a body of information used by the QA application 212 to generate answers to cases. For example, the corpus 214 may contain scholarly articles, dictionary definitions, encyclopedia references, and the like. Critical data store 215 stores a mapping between question context and critical data (also referred to as features) which are highly predictive in generating a response to the question, such that the critical data may be identified when processing additional questions containing the same context. Stated differently, the critical data store 215 specifies data elements that are known to predict confidence in answers generated for classes of question beyond a specified threshold. If the critical data is not present in the question, the QA application 212 may supply known values for the critical data, and process each variant of the question (without a value for the critical data, and with each known value for the critical data). Machine learning (ML) models 216 are models created by the QA application 212 during the training phase, which are used during a runtime pipeline to score and rank candidate answers to cases based on features previously generated for each answer. Evidence classification 217 stores relationships between evidence from the corpus 214, the question context, and the critical data 215.

Figure 3:
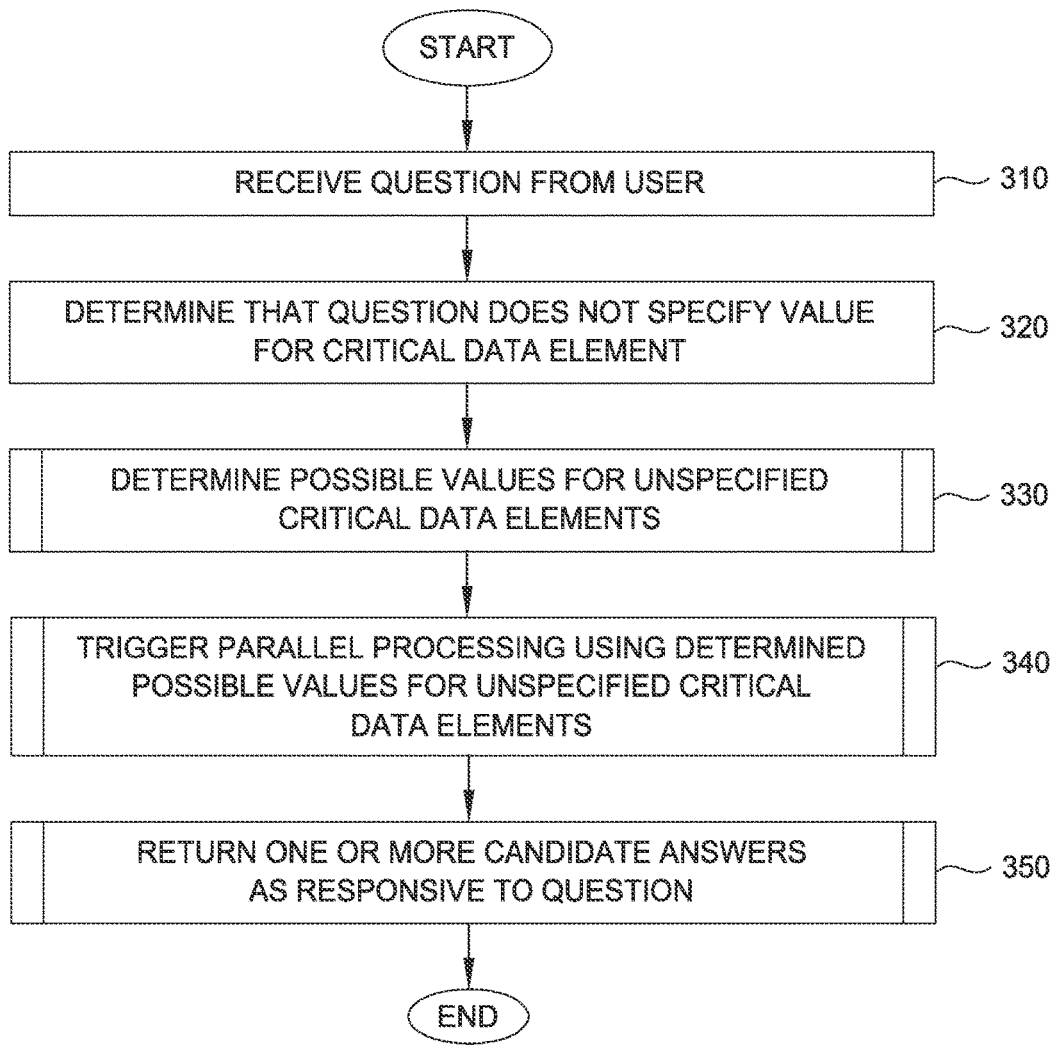
FIG. 3 is a flow chart illustrating a method for question resolution processing in deep question answering systems, according to one embodiment.

FIG. 3 is a flow chart illustrating a method 300 for question resolution processing in deep question answering systems, according to one embodiment. Generally, the QA application 212 may execute the steps of the method 300 in order to identify questions that do not specify values for critical data elements, and trigger parallel processing of the questions supplying alternate values for the critical data elements in order to produce higher quality responses to the questions. At step 310, the QA application 212 receives a question from the user. Generally, the user may ask any type of question. The question may read, for example and without limitation, "what is this patient's risk of developing breast cancer?" At step 320, the QA application 212 may determine that the question does not specify a value for a critical data element. For example, the QA application 212 may reference the critical data store 215 and determine that whether or not the patient has a mutation in the BRCA1 or BRCA2 genes has been determined to impact a confidence of the responses to the question that the QA application 212 may generate.

At step 330, described in greater detail with reference to FIG. 4, the QA application 212 may determine the different possible values for the unspecified critical data elements. In this example, the QA application 212 may determine that the possible values are "yes" and "no" for each of the BRCA1 and BRCA2 mutations. Because the possible values are finite and do not exceed a specified threshold, the QA application 212 may trigger parallel processing of the question using determined possible values for the unspecified critical data elements at step 340, which is described in greater detail with reference to FIG. 5. Generally, at step 340, the QA application 212 may process the question as received from the user, as well as with all permutations (four, in this example) of the values for BRCA1 and BRCA2 mutations. At step 350, described in greater detail with reference to FIG. 6, the QA application 212 may return one or more candidate answers as responsive to the question. Generally, the QA application 212 may return any type or form of output as responsive to the question.

Figure 4:
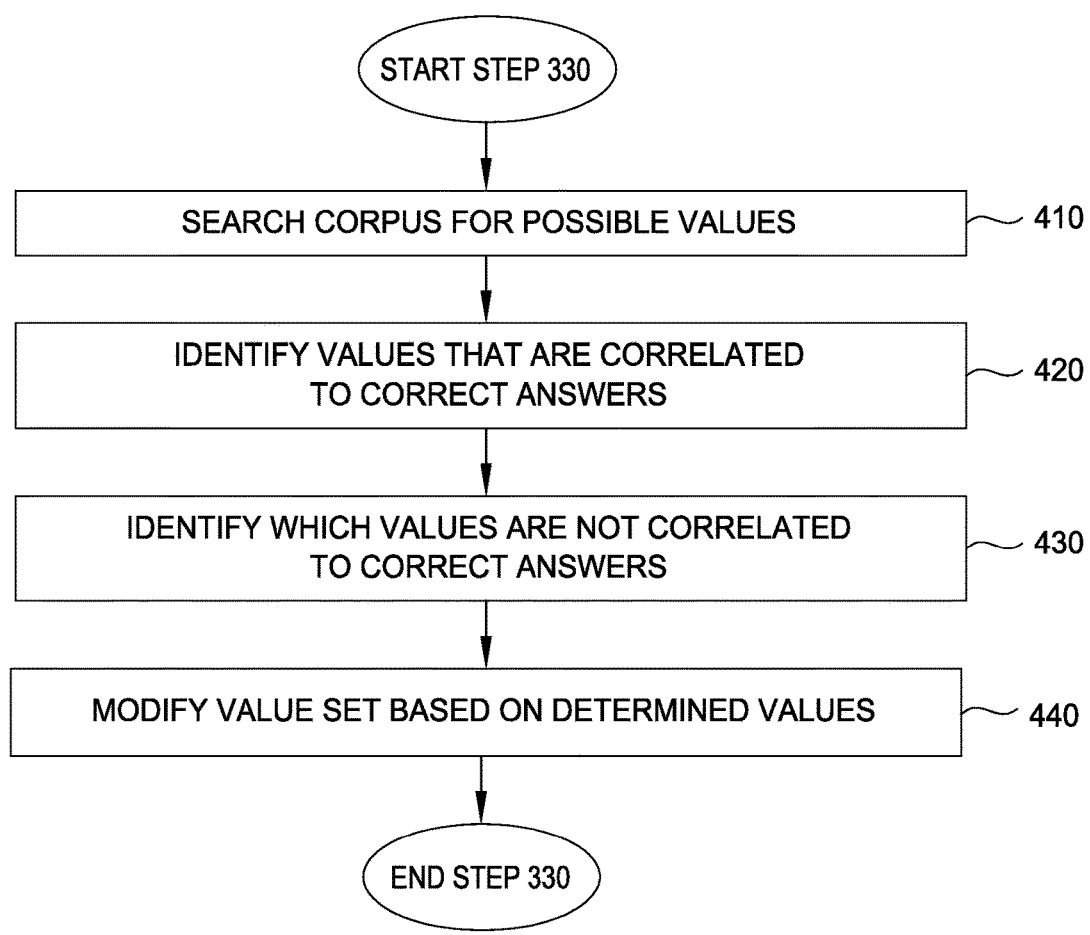
FIG. 4 is a flow chart illustrating a method to determine possible values for data elements, according to one embodiment.

FIG. 4 is a flow chart illustrating a method 400 corresponding to step 330 to determine possible values for data elements, according to one embodiment. Generally, the QA application 212 executes the steps of the method 400 in order to identify and refine the different sets of possible values for all types of data elements. While in some embodiments, a user may define alternate values in the values 210, in many cases, the user may not know all possible values, the ranges of values, and the like. At step 310, the QA application 212 may search the corpus 214 for values for the critical data. Generally, the QA application 212 may search for relevant evidence which states that a particular value may or may not be correlated, or relevant, to a particular question. At step 320, the QA application 212 may identify values that are correlated to correct answers for the given type of question. For example, a medical study may state that "men aged 20-25 experienced an increased risk for automobile related injuries." As such, the QA application 212 may determine that the age range 20-25 is relevant for questions directed to similar subjects. The ranges may be any acceptable value, including, without limitation, specific numbers, ranges, words, concepts, and the like. At step 330, the QA application 212 may determine what values are not correlated to correct answers. For example, a study may indicate that "adults" are at a higher risk for cancer, while specific ages are not relevant. Therefore, values that include specific ages or age ranges may not be required for this particular type of question. At step 340, the QA application 212 may store, modify, or delete values in the values 210 based on the determinations made in steps 310-330. Generally, the QA application 212 may execute the steps of the method 300 as frequently as necessary to maintain an accurate set of values.

Figure 5:
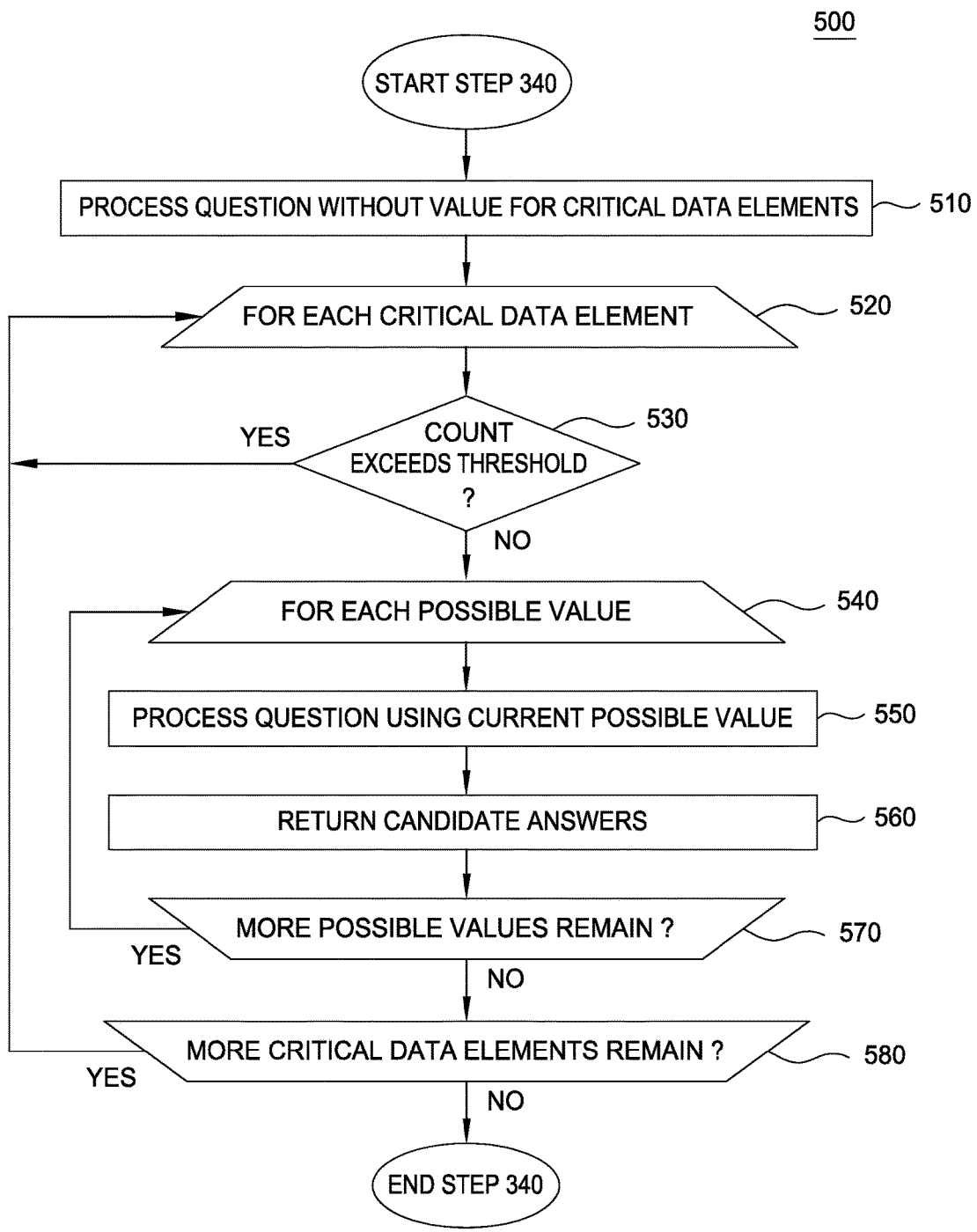
FIG. 5 is a flow chart illustrating a method to trigger parallel processing using determined values for an unspecified data element, according to one embodiment.

FIG. 5 is a flow chart illustrating a method 500 corresponding to step 340 to trigger parallel processing using determined values for an unspecified data element, according to one embodiment. Generally, the QA application 212 may execute the steps of the method 500 in order to produce more accurate results in response to a question that does not specify values for critical data elements. At step 510, the QA application 212 may process the question without the value for one or more critical data elements as received from the user. At step 520, the QA application 212 executes a loop including steps 530-580 for each critical data element. As previously indicated, the critical data element may be a composite of multiple data elements, in which case, the QA application 212 processes permutations of possible values for each component. In at least some embodiments, the QA application 212 may process one or more iterations of the loop in parallel.

At step 530, the QA application 212 determines whether the count of different values for the critical data element exceeds the programmable threshold. If the count exceeds the threshold, the QA application 212 may not process the question in parallel in order to conserve system resources. If the count does not exceed the threshold, the QA application 212 proceeds to step 540, where the QA application 212 executes a loop including steps 550-570 for each possible value for the critical data element. At step 550, the QA application 212 processes the question using the current possible value. Generally, in processing the question using the current possible value, the QA application 212 may perform its traditional processing of questions in order to generate and score candidate answers. At step 560, the QA application 212 returns the candidate answers for the question using the current value, of each of the possible values for the critical data element. At step 570, the QA application 212 determines whether more possible values for the critical data element remain. If more values remain, the QA application 212 returns to step 540. If no more possible values remain, the QA application 212 proceeds to step 580, where the QA application 212 determines whether more critical data elements remain. If more critical data elements remain, the QA application 212 returns to step 520. If no more critical data elements remain the method 500 ends.

Figure 6:
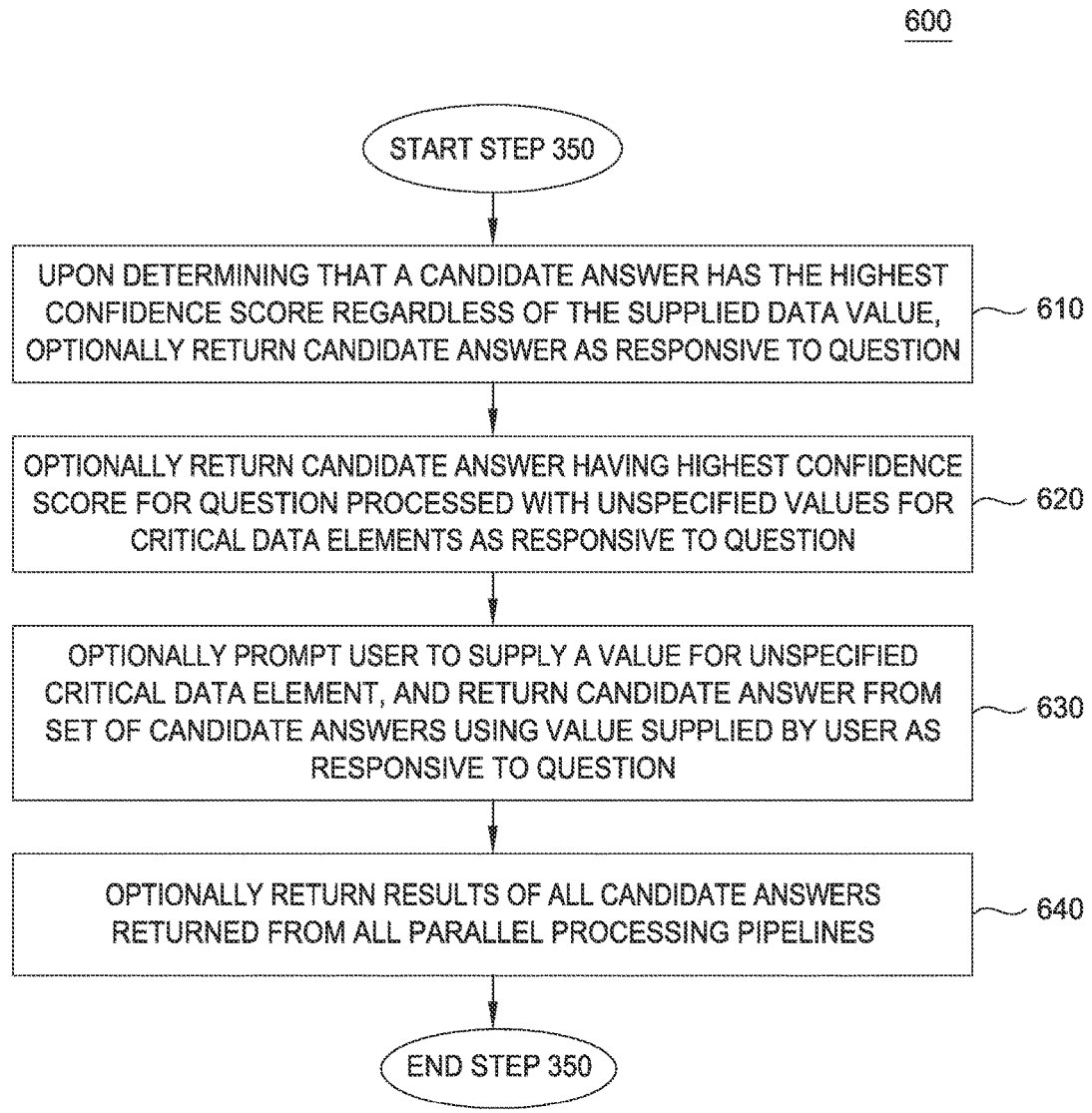
FIG. 6 is a flow chart illustrating a method to return one or more candidate answers as responsive to a question, according to one embodiment.

FIG. 6 is a flow chart illustrating a method 600 corresponding to step 350 to return one or more candidate answers as responsive to a question, according to one embodiment. Generally, the QA application 212 may present the results of the question to the user in any feasible format, and any specific examples described herein should not be considered limiting of the disclosure. In some instances, the QA application 212 may not perform each step of the method 600 in returning results. Furthermore, the QA application 212 may combine one or more of the steps of the method 600 in order to return the results. At step 610, the QA application 212 may return a specific candidate answer as responsive to the question upon determining that the specific candidate answer has the highest confidence score regardless of the supplied value for the critical data element. An example of such a scenario was described above with reference to Table II. At step 620, the QA application 212 may optionally return a candidate answer having the highest confidence score for the question processed with unspecified values for critical data elements as responsive to the question. At step 630, the QA application 212 may optionally prompt the user to supply a value for one or more critical data elements, and return the highest scoring candidate answer from the set of candidate answers using the value supplied by the user as responsive to the question. For example, if the user specifies that he is a "male," then the QA application 212 may return the highest scoring candidate answer for the pipeline that processed the user's question with "male" as the value for gender. At step 640, the QA application 212 may optionally return the results of all candidate answers returned from all parallel processing pipelines. One example of such output is reflected in Table I, above.

Advantageously, embodiments disclosed herein perform parallel processing over multiple paths, supplying different possible values for critical data elements that were not specified by the user. In doing so, deep question answering systems may return more accurate and valuable answers, even if critical information was not specified in the original question. Although additional processing capacity is required to perform the parallel processing, overall, the parallel processing techniques may be more efficient, because the system will not have to completely reprocess the question after the user provides the critical information.

In the foregoing, reference is made to embodiments of the disclosure. However, it should be understood that the disclosure is not limited to specific described embodiments. Instead, any combination of the recited features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access applications or related data available in the cloud. For example, the QA application 212 could execute on a computing system in the cloud and process questions presented by users. In such a case, the QA application 212 could identify unspecified critical data values, identify possible values for the critical data, and store the possible values for the critical data at a storage location in the cloud. Doing so allows a user to access this information from any computing system attached to a network connected to the cloud (e.g., the Internet).

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the foregoing is directed to embodiments of the present disclosure, other and further embodiments of the disclosure may be devised without departing from the basic scope thereof, and the scope thereof is determined by the claims that follow.

What is claimed is:

1. A computer-implemented method, comprising:
receiving, by an interface of a question answering (QA) system, a question not specifying a first element of input data, of a plurality of elements of input data specified in the question;
determining, based on feature classification data generated during a training phase of the QA system, that specifying one possible value of the set of possible values for the first element of input data in the question allows the QA system to: (i) increase a confidence score of at least one candidate answer generated for the question without the value for the first element of input data beyond a specified confidence threshold, and (ii) identify an item of supporting evidence that is not identifiable without the value for the first element of input data;

identifying a set of possible values for the first element of input data, wherein the set of possible values is a finite set of possible values including a first possible value and a second possible value;

generating, by the QA system, a plurality of sets of candidate answers for the question, the plurality of sets of candidate answers comprising: (i) a first set of candidate answers generated without using any of the possible values for the first element of input data, (ii) a second set of candidate answers generated using the first possible value for the first element of input data, (iii) a third set of candidate answers generated using the second possible value for the first element of input data, and (iv) a respective set of candidate answers generated using each remaining possible value in the set of possible values for the first element of input data; and returning at least one candidate answer having a confidence score exceeding the specified confidence threshold from at least one set of candidate answers as responsive to the question.

2. The method of claim 1, wherein the set of possible values for the first element of input data are identified in a corpus of information, wherein the feature classification data comprises a mapping between the first element of input data and a class of questions.

3. The method of claim 2, further comprising:
prior to generating the respective sets of candidate answers:
determining that a count of the possible values in the set of possible values for the first element of input data does not exceed a maximum threshold; and
determining that the received question is of the first class of questions.

4. The method of claim 1, further comprising:
determining, based on the feature classification data, that at least one of the set of possible values for the first element of input data, allows the QA system to identify a candidate answer that is not identifiable when the value for the first element of input data is not included in the question.

5. The method of claim 1, further comprising:
subsequent to returning the at least one candidate answer, receiving by the interface a value for the first element of input data from a user.

6. The method of claim 1, wherein returning at least one candidate answer from at least one of the sets of candidate answers as responsive to the question comprises:
determining that a first candidate answer included in each respective set of candidate answers generated for the question with each possible value in the set of possible values for the first element of input data, has a confidence score greater than a confidence score for all other candidate answers in each respective set of candidate answers; and
returning the first candidate answer as responsive to the question.

7. The method of claim 1, wherein a subset of the candidate answers of a subset of the respective sets of candidate answers are returned as responsive to the question.

8. The method of claim 1, wherein the QA system generates the feature classification data during the training phase by processing a plurality of other questions prior to receiving the question from the interface, wherein the training phase generates a machine learning model specifying the feature classification data.

* * * * *